United States Patent
Chi et al.

(10) Patent No.: US 8,957,208 B1
(45) Date of Patent: Feb. 17, 2015

(54) HETEROLEPTIC IRIDIUM COMPLEX BEARING DIAZOLATE CHELATE

(71) Applicant: National Tsing Hua University, Hsinchu (TW)

(72) Inventors: Yun Chi, Hsinchu (TW); Jia-Ling Liao, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 14/277,182

(22) Filed: May 14, 2014

(30) Foreign Application Priority Data

Jan. 15, 2014 (TW) ............... 103101456 A

(51) Int. Cl.
C07F 15/00 (2006.01)
H01L 51/00 (2006.01)
(52) U.S. Cl.
CPC .................. H01L 51/0085 (2013.01)
USPC .............................. 546/2; 548/101
(58) Field of Classification Search
USPC .............................. 546/2; 548/101
See application file for complete search history.

(56) References Cited

U.S. PATENT DOCUMENTS

2013/0296567 A1* 11/2013 Chi et al. .................. 546/2

* cited by examiner

*Primary Examiner* — Charanjit Aulakh
(74) *Attorney, Agent, or Firm* — Birch, Stewart, Kolasch & Birch, LLP

(57) ABSTRACT

A heteroleptic iridium complex of a formula (I):

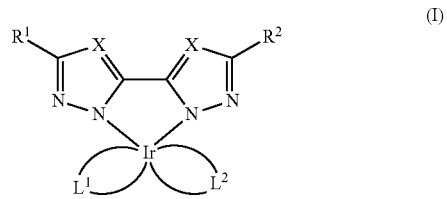

where
$R^1$ and $R^2$ are each independently hydrogen, alkyl, fluoroalkyl, or aryl,
X is $C-X^1$ or nitrogen, $X^1$ being hydrogen or phenyl,
$L^1$ is a monoanionic bidentate ligand, and
$L^2$ is a neutral bidentate ligand.

8 Claims, 1 Drawing Sheet

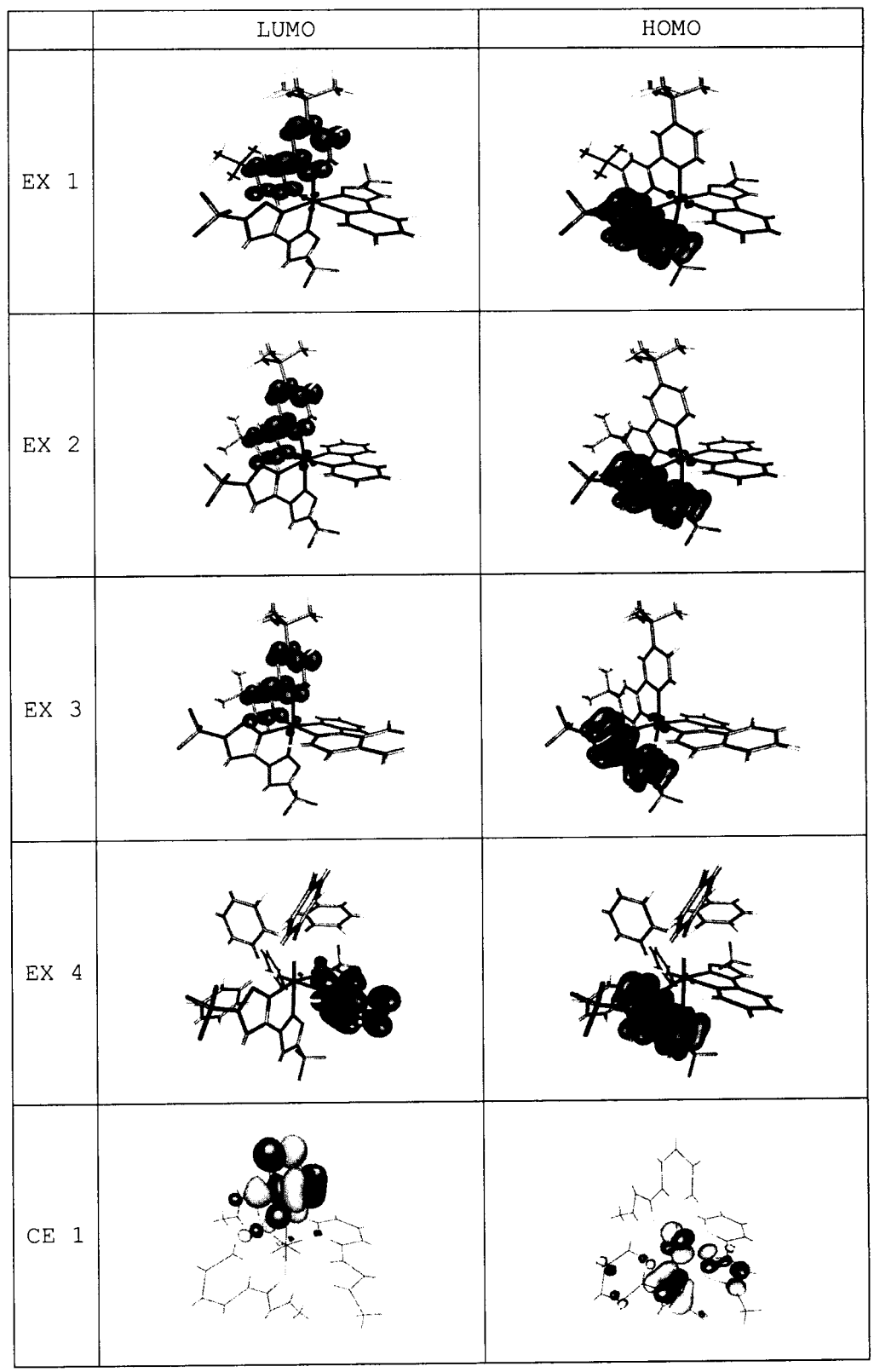

HETEROLEPTIC IRIDIUM COMPLEX BEARING DIAZOLATE CHELATE

CROSS-REFERENCE TO RELATED APPLICATION

This application claims priority of Taiwanese application no. 103101456, filed on Jan. 15, 2014.

BACKGROUND OF THE INVENTION

1. Field of the Invention

This invention relates to a heteroleptic iridium complex for an organic light-emitting diode, more particularly to a heteroleptic iridium complex having a dianionic bidentate ligand and used for phosphorescent organic light-emitting diode (OLED) devices.

2. Description of the Related Art

Organic electroluminescence devices have been applied in the fabrication of flat panel displays in recent years due to their spontaneous emission of light, high efficiency, energy-saving characteristics, low operation voltage, etc. An organic electroluminescence device normally includes an organic light-emitting diode (OLED) and a driving element. An OLED includes an anode, a cathode, and an organic layer disposed between the electrodes for generation of light when a voltage is applied between the anode and the cathode. Generally, the organic layer is made from a phosphorescent material, in which both the singlet and triplet excitons can be harvested and the internal quantum efficiency can reach as high as 100% by utilizing both of the generated excitons. As such, it is desirable to improve both the preparation and the fundamental characteristics of phosphors so as to enhance the light-emitting efficiency of OLEDs. Phosphorescent iridium complexes have been disclosed in, for example, US 2011/0282059 A1, and an article entitled "Homoleptic Tris (Pyridyl Pyrazolate) Ir$^{III}$ Complexes: En Route to Highly Efficient Phosphorescent OLEDs" (Chem. Eur. J. 2010, 16, 4315-4327). In these two documents, two classes of phosphorescent iridium complexes such as homoleptic and heteroleptic iridium complexes are discussed.

For example, a complex of the following formula (a) is a homoleptic iridium complex (formula EM-1 disclosed in US 2011/0282059 A1), and a complex of the following formula (b) is a heteroleptic iridium complex (formula EM-4 disclosed in US 2011/0282059 A1):

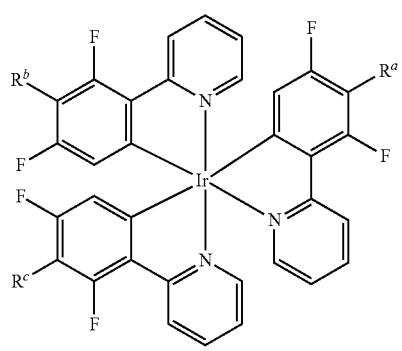

(a)

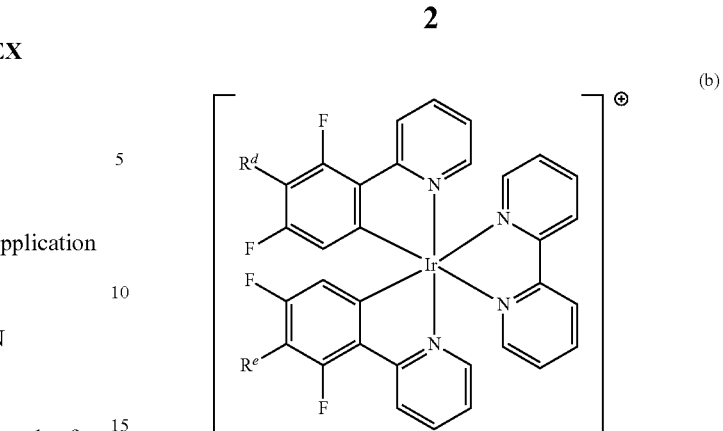

(b)

where, $R^a$ to $R^e$ are

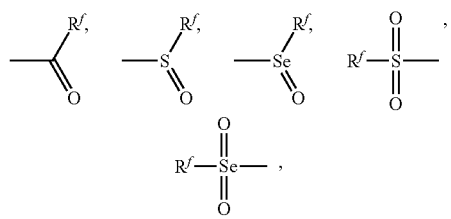

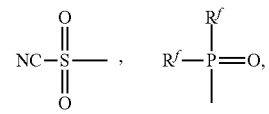

and

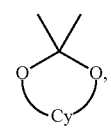

respectively, $R^f$ is $C_1$ to $C_{20}$ alkyl or $C_1$ to $C_{20}$ alkoxy, and

Cy is a $C_1$ to $C_4$ carbocyclic ring, or a $C_1$ to $C_4$ heterocyclic ring.

In the homoleptic iridium complex of formula (a), all the ligands are the same, and thus, it is difficult to fine-tune the energy gap between the highest occupied molecular orbital (HOMO) and the lowest unoccupied molecular orbital (LUMO) and hence, tuning of the emission wavelength. The heteroleptic iridium complex of formula (b) is an ionic iridium complex which is liable to be left on the silica gel column during a separation process (i.e., silica gel column chromatography) and thus has a low product yield. In addition, the ionic iridium complex has poor volatility so that the organic layer cannot be formed by a conventional vacuum deposition process, and needs to be formed by a solution (or wet-printing) process which may render the light-emitting efficiency of the OLED lower.

SUMMARY OF THE INVENTION

An object of the present invention is to provide a novel heteroleptic iridium complex in which a suitable energy gap can be formed between the highest occupied molecular orbital (HOMO) and the lowest unoccupied molecular orbital (LUMO) of different bidentate ligands.

Accordingly, a heteroleptic iridium complex of this invention has the following formula (I):

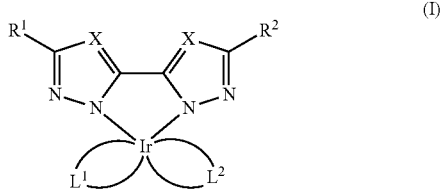

(I)

where
$R^1$ and $R^2$ are each independently hydrogen, alkyl, fluoroalkyl, or aryl,
X is $C\text{-}X^1$ or nitrogen, $X^1$ being hydrogen or phenyl,
$L^1$ is a monoanionic bidentate ligand, and
$L^2$ is a neutral bidentate ligand.

BRIEF DESCRIPTION OF THE DRAWINGS

FIG. 1 shows LUMO and HOMO for Examples 1 to 4.

DETAILED DESCRIPTION OF THE PREFERRED EMBODIMENTS

A heteroleptic iridium complex bearing diazolate chelate of the preferred embodiment of this invention has a formula (I):

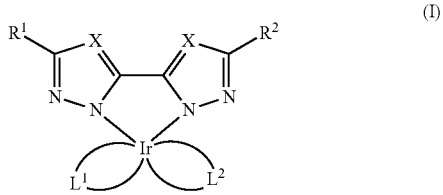

(I)

where
$R^1$ and $R^2$ are each independently hydrogen, alkyl, fluoroalkyl, or aryl, X is $C\text{-}X^1$ or nitrogen, $X^1$ being hydrogen or phenyl, $L^1$ is a monoanionic bidentate ligand, and $L^2$ is a neutral bidentate ligand.

The heteroleptic iridium complex is electroneutral. Thus, the highest occupied molecular orbital (HOMO) of the complex is mainly determined by the dianionic bidentate ligand of a formula of

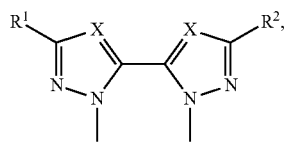

and the lowest unoccupied molecular orbital (LUMO) is mainly determined by $L^1$ or $L^2$. Thus, the energy gap between the HOMO and the LUMO can be determined by selection of reactants for forming the ligands of the heteroleptic iridium complex. As a result, it is expected that the HOMO and LUMO levels can be easily fine-tuned by proper modification of the said ligands respectively.

In other words, when a specific dianionic bidentate ligand is selected, the emission color of the heteroleptic iridium complex can be desirably tuned by modification of the attached substituents (and/or skeletal arrangement) of the monoanionic bidentate ligand ($L^1$) or the neutral bidentate ligand ($L^2$). Thus, in this invention, it is possible to fine-tune the energy gap between the HOMO and the LUMO of the heteroleptic iridium complex and, hence, the associated emission wavelength.

Preferably, X is C—H, and $R^1$ and $R^2$ are each fluoroalkyl.
Preferably, $L^1$ is

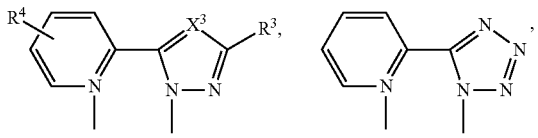

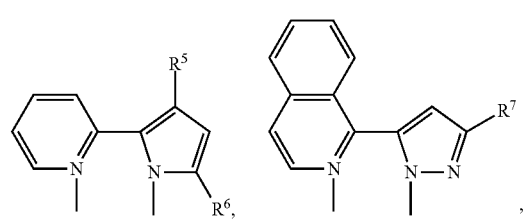

or

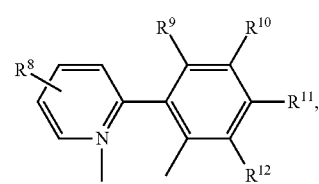

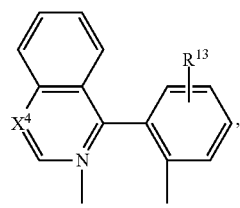

where
$R^3$, $R^6$, $R^5$, and $R^7$ are each independently hydrogen, fluoroalkyl, tert-butyl, or phenyl, $R^4$, $R^8$, and $R^{13}$ are each independently hydrogen or tert-butyl, $R^9$ to $R^{12}$ are each independently hydrogen or fluorine, $X^3$ is nitrogen or $C\text{-}X^1$, and $X^4$ is $C\text{-}X^1$.

$L^2$ is

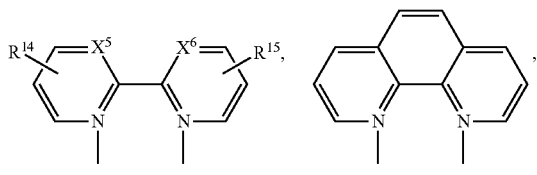

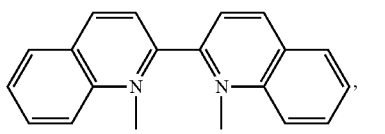

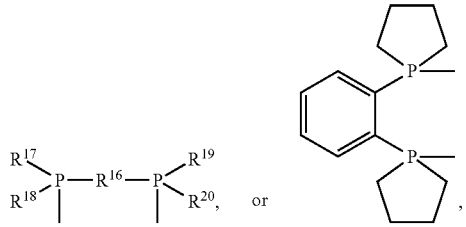

where, $R^{14}$ and $R^{15}$ are each independently hydrogen or tert-butyl, $R^{16}$ is phenylene, ethylene, alkylene, or alkenylene, $R^{17}$ to $R^{20}$ are each independently substituted or unsubstituted phenyl, alkyl, or cycloalkyl, and $X^5$ and $X^6$ are each independently C-$X^1$.

For example, a non-limiting example of the substituted phenyl is fluorine-substituted phenyl.

When $L^2$ is

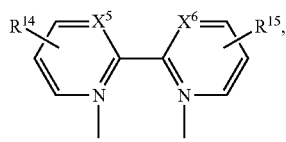

$L^1$ is preferably

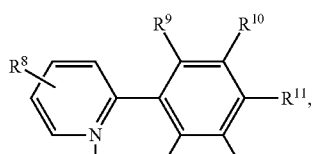

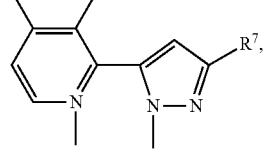

or

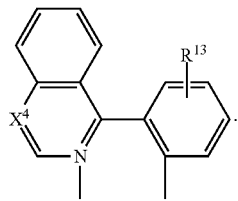

More preferably, $R^7$ to $R^{13}$ are each hydrogen, $R^{14}$ and $R^{15}$ are each tert-butyl, and $X^4$ to $X^6$ are each C-H.

When $L^1$ is

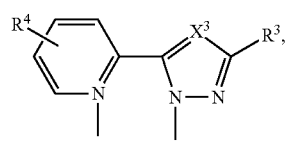

$L^2$ is preferably

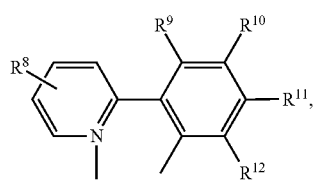

More preferably, $R^3$ is fluoroalkyl, $R^4$ is hydrogen, $R^{14}$ and $R^{15}$ are each tert-butyl, $R^{16}$ is phenylene, $R^{17}$ to $R^{20}$ are each phenyl, and $X^5$ and $X^6$ are each C-H.

When $L^1$ is

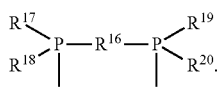

$L^2$ is preferably

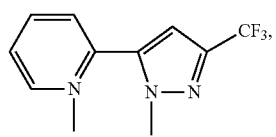

More preferably, $R^8$ is tert-butyl, $R^{16}$ is phenylene, and $R^{17}$ to $R^{20}$ are each phenyl.

In this preferred embodiment, $L^1$ is

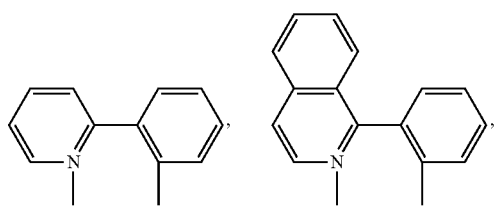

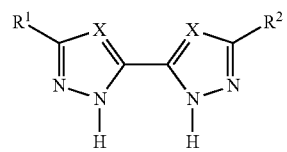

where $R^1$, $R^2$ and X are the same as those defined above.

When $R^1$ and $R^2$ are each aryl or alkyl, hydrogen ions are more liable to dissociate from the central metal atom of the biazole-based compound, thereby enhancing reactivity of the formed biazole-based compound. In addition, when $R^1$ and $R^2$ are each fluoroalkyl, they provide adequate steric hindrance to improve the overall stability, to reduce self-quenching and triplet-triplet annihilation (TTA) at the electrical excited energy states and hence, to achieve a higher emission efficiency for phosphorescent organic light-emitting diodes.

Furthermore, when $R^1$ and $R^2$ are each fluoroalkyl and provide steric hindrance to prevent TTA, the solubility of the heteroleptic iridium complex can be improved and thus, the heteroleptic iridium complex can be separated and purified more easily.

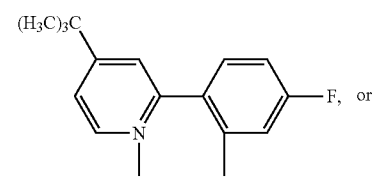

Moreover, due to the distinctive electron withdrawing and donating properties of the $R^1$, $R^2$ substituents in the dianionic bidentate ligand, an energy level of the highest occupied molecular orbital (HOMO) of the complex can be increased (or decreased) for the dianionic bidentate ligand, thereby to increase (or decrease) the energy gap between the HOMO that was mainly determined by the dianionic bidentate ligand and the LUMO that was mainly contributed by the $L^1$ or $L^2$ chelates to a certain extent that the wavelength of the resultant emission can fall within the visible range.

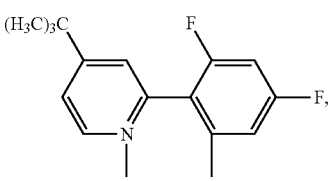

Preferably, the preceding compound for forming the monoanionic bidentate ligand ($L^1$) of the heteroleptic iridium complex is and $L^2$ is

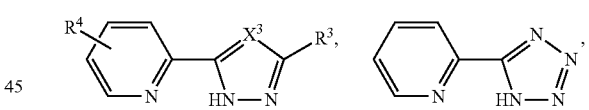

The heteroleptic iridium complex can be synthesized using adequate reactants and under adequate conditions so as to permit the heteroleptic iridium complex to have desired ligands. In this embodiment, the heteroleptic iridium complex is made by the steps of: (1) mixing an iridium source material with two compounds that are used for forming the desired monoanionic bidentate ligand ($L^1$) and the neutral bidentate ligand ($L^2$), respectively; (2) heating the mixture to permit a reaction to occur so as to obtain an intermediate product; and (3) heating a mixture including the intermediate product, a solvent and a biazole-based compound to permit a reaction to occur in the presence of a catalyst, thereby obtaining the heteroleptic iridium complex. The biazole-based compound has been disclosed in the applicant's co-pending application (US 2013/0296567 A1) which is incorporated herein by reference for all purposes. The biazole-based compound has the following formula (II):

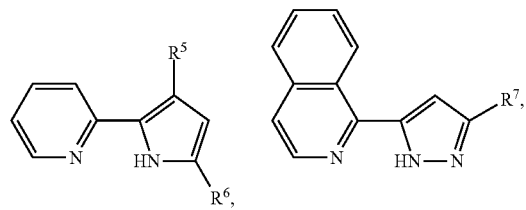

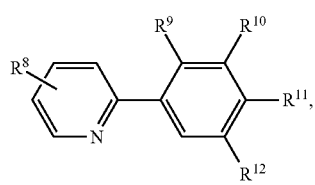

or

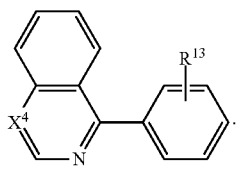

$R^3$ to $R^{13}$ and $X^3$ to $X^4$ are the same as those defined above.

Preferably, the compound for forming the neutral bidentate ligand ($L^2$) of the heteroleptic iridium complex is

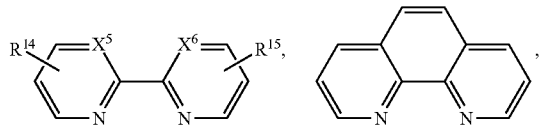

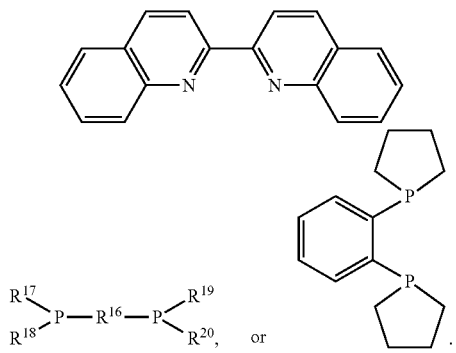

$R^{14}$ to $R^{20}$ and $X^5$ to $X^6$ are the same as those defined above.

The iridium source material is iridium(III) chloride hydrate or trichlorotris (tetrahydrothiophene) iridium(III) ($IrCl_3(THT)_3$). The solvent can be any solvent that can dissolve the intermediate and the biazole-based compound, or any solvent that permits the reaction between the intermediate and the biazole-based compound to be carried out in a homogeneous phase. Non-limiting examples of the solvent include diethylene glycol monomethyl ether, dimethylformamide, decalin, etc. The catalyst is used for promoting the reaction between the intermediate product and the biazole-based compound. Non-limiting examples of the catalyst include sodium hydride, sodium carbonate, etc.

The present invention will now be explained in more detail below by way of the following examples and comparative examples.

Preparation of Biazole-based Compound

<Synthesis Example 1>

Oxalyl dihydrazide (1.00 g, 85 mmol) and trifluoroacetamidine (2.37 g, 21.2 mmol) were placed in a 150 ml reaction flask, followed by addition of 100 ml ethanol to obtain a mixture. The mixture was heated under reflux and under a nitrogen atmosphere for a period of 24 hours. After the reaction was completed and the temperature was cooled down to room temperature, the mixture was subjected to a filtration process to collect a white filter cake, which was then washed using deionized water. Next, the filter cake was placed in a 50 ml reaction flask, was heated to and maintained at 280° C. for 2 hours, and then was subjected to a reduced pressure sublimation process to obtain a white solid product (0.968 g, 3.56 mmol, 42% yield).

The spectrum analysis for the white solid product is: $^{19}F$-($^{1}H$) NMR (470 MHz, $d_6$-dimethyl sulfoxide, 294 K), δ(ppm): −65.80 (s, $CF_3$); MS (EI): m/z 272 $[M]^+$. The chemical structure of the white solid product was confirmed to be

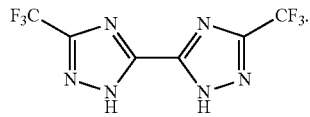

<Synthesis Example 2>

Sodium ethoxide (0.87 g, 12.79 mmol) and anhydrous tetrahydrofuran (THF, 100 ml) were added into a 250 ml reaction flask, followed by slow addition of ethyl trifluoroacetate (1.816 g, 12.78 mmol) and 2,3-butanedione (0.5 g, 5.81 mmol) at 0° C. to obtain a mixture. The mixture was allowed to react at room temperature for a period of 24 hours. After the reaction was completed, pH of the mixture was adjusted to about 7 using a hydrogen chloride solution (2N), followed by removal of THF by reduced pressure distillation to obtain a distilled mixture. Then, the distilled mixture was added with 100 ml ethanol and hydrazine (1.45 g, 29 mmol), and was heated under reflux and under a nitrogen atmosphere for a period of 24 hours. After the reaction was completed, ethanol in the distilled mixture was removed by reduced pressure distillation. Next, 100 ml ethyl acetate and 100 ml deionized water were added to perform partition extraction, and the ethyl acetate layer was collected and further added with 100 ml deionized water, followed by repeating the partition extraction step three times. The collected ethyl acetate layer was subjected to silica gel column chromatography, in which a mixture of ethyl acetate and hexane (ethyl acetate:hexane=1:1) was used as an eluent, followed by recrystallization from dichloromethane to obtain a white solid product (0.43 g, 28% yield).

The spectrum analysis for the white solid product is $^{1}H$ NMR (400 MHz, $d_6$-acetone, 298 K), δ(ppm): 13.53 (s, 2H), 7.16 (s, 2H); MS (EI): m/z 270 $[M]^+$. The chemical structure of the white solid product was confirmed to be

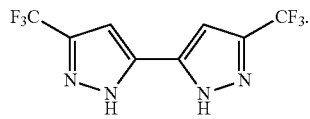

Preparation of Iridium Complex

Example 1 (EX 1)

Iridium(III) chloride hydrate (150 mg, 0.43 mmol) was placed in a round-bottom flask, and

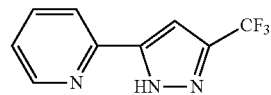 [SMILES: FC(F)(F)c1cc(-c2ccccn2)[nH]n1]

(91 mg, 0.43 mmol) and

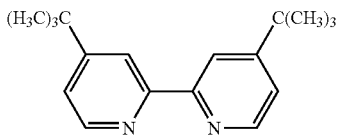

(115 mg, 0.43 mmol) were added thereto. Thereafter, 15 ml diethylene glycol monomethyl ether was added to the round-bottom flask to obtain a mixture. The mixture was heated to and maintained at 160° C. under a nitrogen atmosphere for a period of 12 hours. After the reaction was completed and the temperature was reduced to room temperature, diethylene glycol monomethyl ether in the mixture was removed by reduced pressure distillation to obtain a yellow solid. The yellow solid was subjected to silica gel column chromatography, in which a mixture of ethyl acetate and hexane (ethyl acetate:hexane=2:1) was used as an eluent for the silica gel column. The eluent was collected, and the solvent in the eluent was removed by concentration to obtain an intermediate product (115 mg, 34% yield).

The spectrum analysis for the intermediate product is: $^1$H NMR (400 MHz, CDCl$_3$, 298K), δ(ppm): 9.87 (d, J=6.0 Hz, 1H), 9.67 (d, J=6.0 Hz, 1H), 8.02 (s, 1H), 7.91 (s, 1H), 7.89 (t, J=8.0 Hz, 1H), 7.75 (d, J=8.0 Hz, 1H), 7.69 (d, J=6.0 Hz, 1H), 7.48 (d, J=6.0 Hz, 1H), 7.36 (t, J=6.8 Hz, 1H), 7.19 (d, J=1.6 Hz, 1H), 6.81 (s, 1H), 1.49 (s, 9H), 1.35 (s, 9H); $^{19}$F NMR (400 MHz, CDCl$_3$, 298K), δ(ppm): −60.48 (s, 3F).

The chemical structure of the intermediate product was confirmed to be

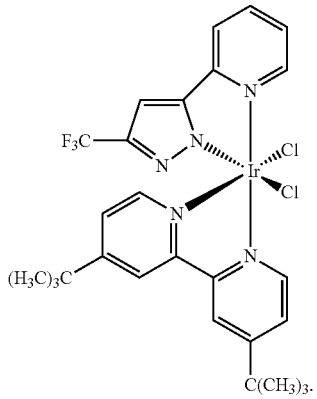

The product of Synthesis Example 2 (40 mg) was dissolved in 5 ml anhydrous THF to obtain a THF solution. Sodium hydride (8 mg, 0.33 mmol) was disposed in a round-bottom flask, and 5 ml anhydrous THF was added thereto, followed by mixing with the THF solution for 20 minutes in an ice bath to obtain the first solution. The intermediate product (100 mg, 0.13 mmol) was disposed in a 25 ml two-neck flask, and 10 ml diethylene glycol monomethyl ether was added thereto to obtain a second solution. The first solution was added to the second solution to obtain a mixture solution, and the mixture solution was heated to and maintained at 160° C. under a nitrogen atmosphere for a period of 12 hours. After the reaction was completed and the temperature was reduced to room temperature, the solvent in the mixture solution was removed by reduced pressure distillation to obtain a yellow solid. The yellow solid was subjected to silica gel column chromatography, in which a mixture of ethyl acetate and hexane (ethyl acetate:hexane=1:2) was used as an eluent for the silica gel column. The eluent was collected, and the solvent in the eluent was removed by concentration, followed by recrystallization from a mixture of ethyl acetate and hexane to obtain a green solid (52 mg, 40% yield) (hereinafter referred to as heteroleptic iridium complex A-1).

The spectrum analysis for the heteroleptic iridium complex A-1 is: $^1$H NMR (400 MHz, CDCl$_3$, 298 K), δ(ppm): 8.05 (d, J=2.0 Hz, 1H), 8.00 (d, J=2.0 Hz, 1H), 7.69 (td, J=8, 1.2 Hz, 1H), 7.62 (d, J=6.4 Hz, 2H), 7.58 (d, J=6.4 Hz, 1H), 7.41 (dd, J=6.4, 2 Hz, 1H), 7.30 (dd, J=6.4, 2 Hz, 1H), 7.13 (d, J=5.6 Hz, 1H), 6.99 (td, J=6.4, 1.2 Hz, 1H), 6.64 (s, 1H), 6.58 (s, 1H), 6.57 (s, 1H), 1.41 (s, 18H); $^{19}$F NMR (400 MHz, CDCl$_3$, 298 K), δ(ppm): −60.11 (s, 3F), −60.13 (s, 3F), −60.32 (s, 3F).

The chemical structure of the heteroleptic iridium complex A-1 was confirmed to be

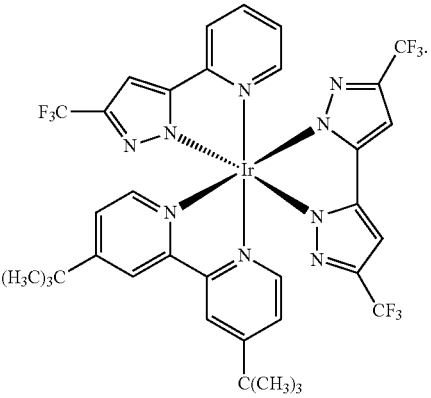

Example 2 (EX 2)

Iridium(III) chloride hydrate (222 mg, 0.63 mmol) was placed in a round-bottom flask, and

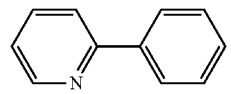 [SMILES: c1ccc(-c2ccccn2)cc1]

(98 mg, 0.63 mmol) and

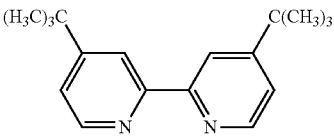

(168 mg, 0.63 mmol) were added thereto. Thereafter, 15 ml diethylene glycol monomethyl ether was added to the round-bottom flask to obtain a mixture. The mixture was heated to and maintained at 160° C. under a nitrogen atmosphere for a period of 12 hours. After the reaction was completed and the temperature was reduced to room temperature, diethylene glycol monomethyl ether in the mixture was removed by reduced pressure distillation to obtain a yellow solid. The yellow solid was subjected to silica gel column chromatography, in which a mixture of ethyl acetate and methanol (ethyl acetate:methanol=10:1) was used as an eluent for the silica gel column. The eluent was collected, and the solvent in the eluent was removed by concentration to obtain an intermediate product (225 mg, 60% yield).

The spectrum analysis for the intermediate product is: $^1$H NMR (400 MHz, CDCl$_3$, 298 K), δ(ppm): 10.00 (d, J=6.0 Hz, 1H), 9.94 (d, J=6.0 Hz, 1H), 7.99 (d, J=1.6 Hz, 1H), 7.88 (m, 2H), 7.77 (t, J=7.6 Hz, 1H), 7.64 (dd, J=6.0, 2.0 Hz, 1H), 7.64 (dd, J=6.0, 2.0 Hz, 1H), 7.60 (d, J=7.7 Hz, 1H), 7.46 (d, J=6.2 Hz, 1H), 7.30 (t, J=6.4 Hz, 1H), 7.05 (dd, J=6.2, 2.0 Hz, 1H), 6.86 (t, J=7.2 Hz, 1H), 6.78 (t, J=7.6 Hz, 1H), 6.17 (d, J=7.6 Hz, 1H), 1.50 (s, 9H), 1.30 (s, 9H).

The chemical structure of the intermediate product was confirmed to be

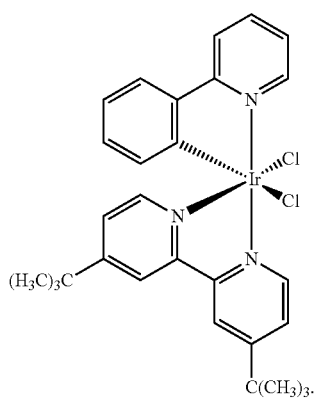

The product of Synthesis Example 2 (62 mg, 0.22 mmol) was dissolved in 5 ml anhydrous THF to obtain a THF solution. Sodium hydride (12 mg, 0.50 mmol) was disposed in a round-bottom flask, and 5 ml anhydrous THF was added thereto, followed by mixing with the THF solution for 20 minutes in an ice bath to obtain a first solution. The intermediate product (150 mg, 0.22 mmol) was disposed in a 25 ml two-neck flask, and 10 ml diethylene glycol monomethyl ether was added thereto to obtain a second solution. The first solution was added to the second solution to obtain a mixture solution, and the mixture solution was heated to and maintained at 160° C. under a nitrogen atmosphere for a period of 12 hours. After the reaction was completed and the temperature was reduced to room temperature, the solvent in the mixture solution was removed by reduced pressure distillation to obtain a yellow solid. The yellow solid was subjected to silica gel column chromatography, in which a mixture of ethyl acetate and hexane (ethyl acetate:hexane=1:2) was used as an eluent for the silica gel column. The eluent was collected, and the solvent in the eluent was removed by concentration, followed by recrystallization from a mixture of dichloromethane and hexane to obtain a yellow solid (149 mg, 78% yield) (hereinafter referred to as heteroleptic iridium complex A-2).

The spectrum analysis for the heteroleptic iridium complex A-2 is: $^1$H NMR (400 MHz, CDCl$_3$, 298 K), δ(ppm): 8.00 (d, J=2.0 Hz, 1H), 7.96 (d, J=2.0 Hz, 1H), 7.64 (d, J=8.4 Hz, 1H), 7.59 (d, J=6.4 Hz, 1H), 7.56 (d, J=6 Hz, 1H), 7.52 (d, J=7.6 Hz, 1H), 7.40 (m, 3H), 7.21 (dd, J=6, 2 Hz, 1H), 6.89 (m, 3H), 1.42 (s, 9H), 1.32 (s, 9H); $^{19}$F NMR (400 MHz, CDCl$_3$, 298 K), δ(ppm): −59.42 (s, 3F), −59.83 (s, 3F).

The chemical structure of the heteroleptic iridium complex A-2 was confirmed to be

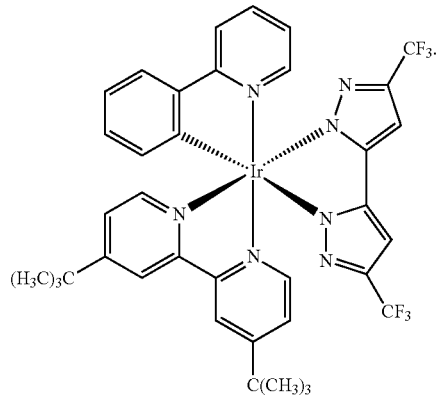

Example 3 (EX 3)

Iridium(III) chloride hydrate (200 mg, 0.57 mmol) was placed in a round-bottom flask, and

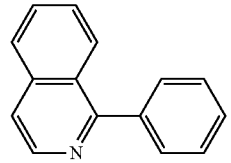 [SMILES: c1ccc(-c2nccc3ccccc23)cc1]

(117 mg, 0.51 mmol) and

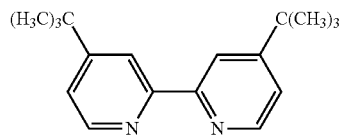

(152 mg, 0.57 mmol) were added thereto. Thereafter, 15 ml diethylene glycol monomethyl ether was added to the round-bottom flask to obtain a mixture. The mixture was heated to and maintained at 160° C. under a nitrogen atmosphere for a period of 12 hours. After the reaction was completed and the temperature was reduced to room temperature, diethylene glycol monomethyl ether in the mixture was removed by reduced pressure distillation to obtain a yellow solid. The yellow solid was subjected to silica gel column chromatography, in which a mixture of ethyl acetate and methanol (ethyl acetate:methanol=10:1) was used as an eluent for the silica gel column. The eluent was collected, and the solvent in the eluent was removed by concentration to obtain an intermediate product (275 mg, 66% yield).

The product of Synthesis Example 2 (101 mg, 0.37 mmol) was dissolved in 5 ml anhydrous THF to obtain a THF solution. Sodium hydride (22 mg, 0.93 mmol) was disposed in a round-bottom flask, and 5 ml anhydrous THF was added thereto, followed by mixing with the THF solution for 20 minutes in an ice bath to obtain a first solution. The intermediate product (275 mg, 0.37 mmol) was disposed in a 25 ml two-neck flask, and 10 ml diethylene glycol monomethyl ether was added thereto to obtain a second solution. The first solution was added to the second solution to obtain a mixture solution, and the mixture solution was heated to and maintained at 160° C. under a nitrogen atmosphere for a period of 12 hours. After the reaction was completed and the temperature was cooled down to room temperature, the solvent in the mixture solution was removed by reduced pressure distillation to obtain an orange-red solid. The orange-red solid was subjected to silica gel column chromatography, in which a mixture of ethyl acetate and hexane (ethyl acetate:hexane=1:1) was used as an eluent for the silica gel column. The eluent was collected, and the solvent in the eluent was removed by concentration, followed by recrystallization from a mixture of dichloromethane and hexane to obtain an orange solid (205 mg, 59% yield) (hereinafter referred to as heteroleptic iridium complex A-3).

The spectrum analysis for the heteroleptic iridium complex A-3 is: $^1$H NMR (400 MHz, CDCl$_3$, 298 K), δ(ppm): 8.89 (d, J=8.8 Hz, 1H), 8.23 (d, J=8.0 Hz, 1H), 8.25 (s, 1H), 8.23 (s, 1H), 7.77 (d, J=7.8 Hz, 1H), 7.62 (m, 4H), 7.46 (d, J=6.4 Hz, 1H), 7.41 (d, J=6.0 Hz, 1H), 7.24 (m, 1H), 7.15 (d, J=6.0 Hz, 1H), 7.09 (t, J=7.2 Hz, 1H), 6.93 (t, J=7.2 Hz, 1H), 6.63 (s, 1H), 6.52 (s, 1H), 6.43 (d, J=7.2 Hz, 1H), 1.45 (s, 9H), 1.35 (s, 9H); $^{19}$F NMR (400 MHz, CDCl$_3$, 298K), δ(ppm): −59.34 (s, 3F), −59.85 (s, 3F).

The chemical structure of the heteroleptic iridium complex A-3 was confirmed to be

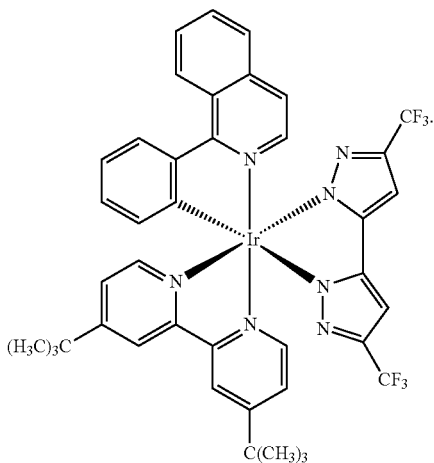

Example 4 (EX 4)

IrCl$_3$(THT)$_3$ (300 mg, 0.63 mmol) was placed in a round-bottom flask, and

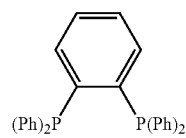

(239 mg, 0.63 mmol) and 20 ml decalin were subsequently added thereto to obtain the first mixture. The first mixture was heated under reflux and under a nitrogen atmosphere for a period of 6 hours. After the reaction was completed and the temperature was reduced to room temperature, decalin in the first mixture was removed by reduced pressure distillation. Thereafter,

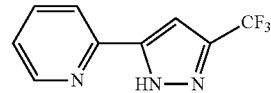 [SMILES: FC(F)(F)c1cc(-c2ccccn2)[nH]n1]

(114 mg, 0.63 mmol) and 15 ml dimethylformamide were sequentially added to the first mixture, in which decalin was removed, to obtain a second mixture. The second mixture was heated under reflux and under a nitrogen atmosphere for a second reaction period of 12 hours. After the reaction was completed and the temperature was cooled down to room temperature, dimethylformamide in the second mixture was removed by reduced pressure distillation to obtain a solid. The solid was subjected to silica gel column chromatography, in which a mixture of ethyl acetate and hexane (ethyl acetate:hexane=2:1) was used as an eluent for the silica gel column. The eluent was collected, and the solvent in the eluent was removed by concentration to obtain an intermediate product (305 mg, 62% yield).

The spectrum analysis for the intermediate product is: $^1$H NMR (400 MHz, CDCl$_3$, 298 K), δ(ppm): 9.23 (t, J=4.4 Hz, 1H), 7.77 (m, 6H), 7.61 (m, 1H), 7.52 (m, 2H), 7.36 (m, 10H), 7.17 (m, 3H), 6.83 (td, J=7.6, 2/4 Hz, 2H), 6.55 (m, 2H), 6.34 (s, 1H); $^{19}$F NMR (400 MHz, CDCl$_3$, 298 K), δ(ppm): −61.21 (s, 3F).

The chemical structure of the intermediate product was confirmed to be

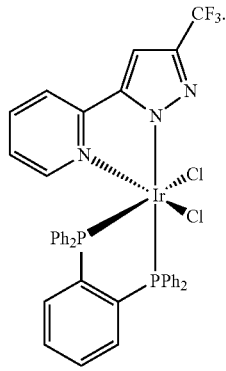

The product of Synthesis Example 2 (62 mg, 0.22 mmol) was dissolved in 5 ml anhydrous THF to obtain a THF solution. Sodium hydride (13 mg, 0.50 mmol) was disposed in a round-bottom flask, and 5 ml anhydrous THF was added thereto, followed by mixing with the THF solution for 20 minutes in an ice bath to obtain a first solution. The intermediate product (150 mg, 0.22 mmol) was disposed in a 25 ml two-neck flask, and 10 ml dimethylformamide was added thereto to obtain a second solution. The first solution was added to the second solution to obtain a mixture solution, and the mixture solution was heated to and maintained at 170° C. under a nitrogen atmosphere for a period of 12 hours. After the reaction was completed and the temperature was reduced to room temperature, the solvent in the mixture solution was removed by reduced pressure distillation to obtain an orange-red solid. The orange-red solid was subjected to silica gel column chromatography, in which a mixture of ethyl acetate and hexane (ethyl acetate:hexane=1:2) was used as an eluent for the silica gel column. The eluent was collected, and the solvent in the eluent was removed by concentration, followed by recrystallization from a mixture of dichloromethane and hexane to obtain a white solid (64 mg, 35% yield) (hereinafter referred to as heteroleptic iridium complex A-4).

The spectrum analysis for the heteroleptic iridium complex A-4 is: $^1$H NMR (400 MHz, CDCl$_3$, 298 K), δ(ppm): 7.9~7.88 (m, 2H), 7.73~7.70 (m, 2H), 7.66~7.62 (m, 4H), 7.48~7.35 (m, 5H), 7.25~7.21 (m, 3H), 7.13 (t, J=7.48 Hz, 1H), 7.08 (t, J=7.48 Hz, 1H), 6.84~6.79 (m, 4H), 6.67~6.59 (m, 4H), 6.50~6.45 (m, 2H), 6.31 (s, 1H), 6.03 (s, 1H), 6.01 (s, 1H); $^{19}$F-{$^1$H} NMR (470 MHz, CDCl$_3$, 294 K), δ(ppm): −60.30 (s, 3F), −60.59 (s, 3F), −61.06 (s, 3F)○$^{31}$P-{$^1$H} NMR (202 MHz, CDCl$_3$, 294 K), δ(ppm): 15.23 (d, J=3.63 Hz, 1P), 16.11 (d, J=3.63 Hz, 1P).

The chemical structure of the heteroleptic iridium complex A-4 was confirmed to be

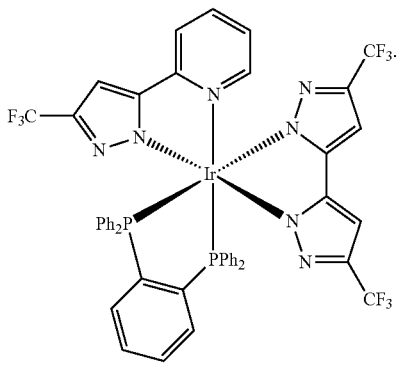

Example 5 (EX 5)

IrCl$_3$(THT)$_3$ (300 mg, 0.63 mmol) was placed in a round-bottom flask,

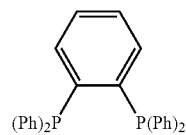

(239 mg, 0.63 mmol) and 20 ml decalin were subsequently added thereto to obtain the first mixture. The first mixture was heated under reflux and under a nitrogen atmosphere for a period of 6 hours. After the reaction was completed and the temperature was reduced to room temperature, decalin in the first mixture was removed by reduced pressure distillation. Thereafter,

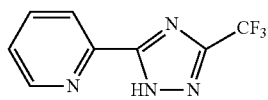

(114 mg, 0.63 mmol) and 15 ml dimethylformamide were sequentially added to the first mixture, in which decalin was removed, to obtain a second mixture. The second mixture was heated under reflux and under a nitrogen atmosphere for a second reaction period of 12 hours. After the reaction was completed and the temperature was reduced to room temperature, dimethylformamide in the second mixture was removed by reduced pressure distillation to obtain a solid. The solid was subjected to silica gel column chromatography, in which a mixture of ethyl acetate and hexane (ethyl acetate:hexane=3:1) was used as an eluent for the silica gel column. The eluent was collected, and the solvent in the eluent was removed by concentration to obtain an intermediate product (294 mg, 60% yield).

The product of Synthesis Example 1 (62 mg, 0.22 mmol) was dissolved in 5 ml anhydrous THF to obtain a THF solution. Sodium hydride (13 mg, 0.50 mmol) was disposed in a round-bottom flask, and 5 ml anhydrous THF was added thereto, followed by mixing with the THF solution for 20 minutes in an ice bath to obtain a first solution. The intermediate product (150 mg, 0.22 mmol) was disposed in a 50 ml two-neck flask, and 10 ml dimethylformamide was added thereto to obtain a second solution. The first solution was added to the second solution to obtain a mixture solution, and the mixture solution was heated to and maintained at 170° C. under a nitrogen atmosphere for a period of 12 hours. After the reaction was completed and the temperature was reduced to room temperature, the solvent in the mixture solution was removed by reduced pressure distillation to obtain an orange-red solid. The orange-red solid was subjected to silica gel column chromatography, in which a mixture of ethyl acetate and hexane (ethyl acetate:hexane=2:1) was used as an eluent for the silica gel column. The eluent was collected, and the solvent in the eluent was removed by concentration, followed by recrystallization from a mixture of dichloromethane and hexane to obtain a white solid (82 mg, 45% yield) (hereinafter referred to as heteroleptic iridium complex A-5).

The spectrum analysis for the heteroleptic iridium complex A-5 is: $^1$H NMR (400 MHz, CDCl$_3$, 294 K), δ(ppm): 7.96 (d, J=8.00 Hz, 1H), 7.84~7.67 (m, 9H), 7.54~7.49 (m, 2H), 7.42 (t, J=6.58 Hz, 2H), 7.34 (t, J=6.58 Hz, 2H), 7.27 (m, 1H), 7.18 (t, J=7.40 Hz, 1H), 7.08 (t, J=6.08 Hz, 1H), 7.03 (m, 1H), 6.95~6.88 (m, 4H), 6.52~6.40 (m, 4H); $^{19}$F-{$^1$H} NMR (470 MHz, CDCl$_3$, 294 K), δ(ppm): −63.95 (s, 3F), −64.17 (s, 3F), −64.40 (s, 3F); $^{31}$P-{$^1$H} NMR (202 MHz, CDCl$_3$, 294K), δ(ppm): 15.03 (d, J=3.23 Hz, 1P), 15.41 (d, J=3.23 Hz, 1P).

The chemical structure of the heteroleptic iridium complex A-5 confirmed to be

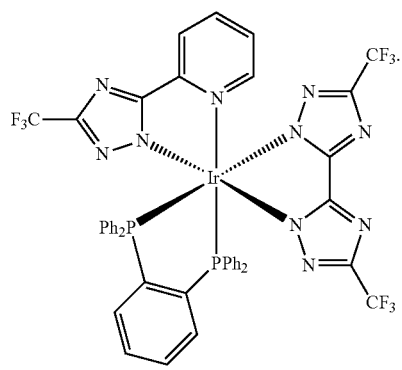

Example 6 (EX 6)

IrCl$_3$(THT)$_3$ (300 mg, 0.63 mmol) was placed in a round-bottom flask,

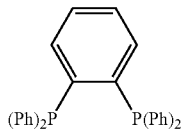

(239 mg, 0.63 mmol) and 20 ml decalin were subsequently added thereto to obtain the first mixture. The first mixture was heated under reflux and under a nitrogen atmosphere for a period of 6 hours. After the reaction was completed and the temperature was reduced to room temperature, decalin in the first mixture was removed by reduced pressure distillation. Thereafter,

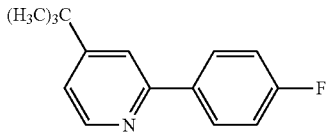

(122 mg, 0.63 mmol) and 15 ml dimethylformamide were sequentially added to the first mixture, from which decalin was removed, to obtain a second mixture. The second mixture was heated under reflux and under a nitrogen atmosphere for a second reaction period of 12 hours. After the reaction was completed and the temperature was cooled down to room temperature, dimethylformamide in the second mixture was removed by reduced pressure distillation to obtain a solid. The solid was washed using diethyl ether to obtain an intermediate product (400 mg, 80% yield).

The product of Synthesis Example 2 (69 mg, 0.25 mmol) was dissolved in 5 ml anhydrous THF to obtain a THF solution. Sodium hydride (15 mg, 0.62 mmol) was disposed in a round-bottom flask, and 5 ml anhydrous THF was added thereto, followed by mixing with the THF solution for 20 minutes in an ice bath to obtain the first solution. The intermediate product (200 mg, 0.22 mmol) was disposed in a 50 ml two-neck flask, and 10 ml dimethylformamide was added thereto to obtain a second. solution. The first solution was added to the second solution to obtain a mixture solution, and the mixture solution was heated to and maintained at 170° C. under a nitrogen atmosphere for a period of 12 hours. After the reaction was completed and the temperature was cooled down to room temperature, the solvent in the mixture solution was removed by reduced pressure distillation to obtain an orange-red solid. The orange-red solid was subjected to silica gel column chromatography, in which a mixture of ethyl acetate and hexane (ethyl acetate:hexane=1:1) was used as an eluent for the silica gel column. The eluent was collected, and the solvent in the eluent was removed by concentration, followed by recrystallization from a mixture of dichloromethane and hexane to obtain a white solid (121 mg, 50% yield) (hereinafter referred to as heteroleptic iridium complex A-6).

The spectrum analysis for the heteroleptic iridium complex A-6 is: $^1$H NMR (400 MHz, CDCl$_3$, 294 K), δ(ppm): 8.05~8.00 (m, 2H), 7.91~7.86 (m, 2H), 7.82~7.78 (m, 4H), 7.59~7.56 (m, 2H), 7.52 (t, J=7.44 Hz, 1H), 7.41 (t, J=7.44 Hz, 1H), 7.33 (t, J=7.60 Hz, 2H), 7.28~7.25 (m, 1H), 7.21~7.12 (m, 4H), 6.85 (td, J=7.78, 2.44 Hz, 2H), 6.78 (td, J=7.78, 2.41 Hz, 2H), 6.69 (td, J=8.64, 2.36 Hz, 1H), 6.44 (s, 1H), 6.34 (s, 1H), 6.13 (m, 4H), 6.01 (d, J=10.84 Hz, 1H), 5.74 (s, 1H), 1.20 (s, 9H); $^{19}$F-{$^1$H} NMR (470 MHz, CDCl$_3$, 294 K), δ(ppm): −58.28 (s, 3F), −58.55 (s, 3F), −111.61 (s, 1F); $^{31}$P-{$^1$H} NMR (202 MHz, CDCl$_3$, 294K), δ(ppm): 18.96 (d, J=4.04 Hz, 1P), 14.28 (d, J=4.04 Hz, 1P).

The chemical structure of the heteroleptic iridium complex A-6 was confirmed to be

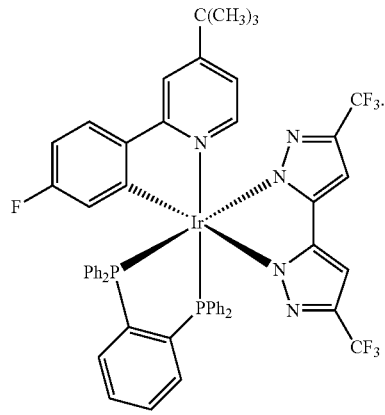

Example 7 (EX 7)

IrCl$_3$(THT)$_3$ (150 mg, 0.27 mmol) was placed in a round-bottom flask,

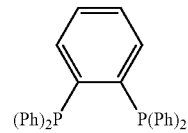

(119 mg, 0.27 mmol), 15 ml decalin, and 15 ml dimethylformamide were subsequently added thereto to obtain the first mixture. The first mixture was heated under reflux and under a nitrogen atmosphere for a period of 6 hours. After the reaction was completed and the temperature was cooled down to room temperature, decalin in the first mixture was removed by reduced pressure distillation. Thereafter,

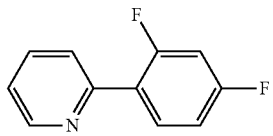 [SMILES: Fc1ccc(-c2ccccn2)c(F)c1]

(51 mg, 0.27 mmol) and 15 ml dimethylformamide were sequentially added to the first mixture, from which decalin was removed, to obtain a second mixture. The second mixture was heated under reflux and under a nitrogen atmosphere for a second reaction period of 12 hours. After the reaction was completed and the temperature was reduced to room temperature, dimethylformamide in the second mixture was removed by reduced pressure distillation to obtain a solid. The solid was washed using diethyl ether to obtain an intermediate product (400 mg, 70% yield).

The product of Synthesis Example 2 (69 mg, 0.25 mmol) was dissolved in 5 ml anhydrous THF to obtain a THF solution. Sodium hydride (15 mg, 0.62 mmol) was disposed in a round-bottom flask, and 5 ml anhydrous THF was added thereto, followed by mix with the THF solution for 20 minutes in an ice bath to obtain a first solution. The intermediate product (198 mg, 0.22 mmol) was disposed in a 50 ml two-neck flask, and 10 ml dimethylformamide was added thereto to obtain a second solution. The first solution was added to the second solution to obtain a mixture solution, and the mixture solution was heated to and maintained at 170° C. under a nitrogen atmosphere for a period of 12 hours. After the reaction was completed and the temperature was reduced to room temperature, the solvent in the mixture solution was removed by reduced pressure distillation to obtain an orange-red solid. The orange-red solid was subjected to silica gel column chromatography, in which a mixture of ethyl acetate and hexane (ethyl acetate:hexane=1:1) was used as an eluent for the silica gel column. The eluent was collected, and the solvent in the eluent was removed by concentration, followed by recrystallization from a mixture of dichloromethane and hexane to obtain a white solid (72 mg, 30% yield) (hereinafter referred to as heteroleptic iridium complex A-7).

The spectrum analysis for the heteroleptic iridium complex A-7 is: $^1$H NMR (400 MHz, CDCl$_3$, 294 K), δ(ppm): 8.21~8.16 (m, 2H), 7.99~7.94 (m, 2H), 7.86~7.79 (m, 2H), 7.71~7.67 (m, 1H), 7.62~7.60 (m, 2H), 7.54~7.48 (m, 2H), 7.44 (t, J=7.88 Hz, 1H), 7.38 (t, J=7.88 Hz, 1H), 7.31 (td, J=7.90, 1.76 Hz, 2H), 7.24 (td, J=7.90, 1.76 Hz, 2H), 7.15 (t, J=7.44 Hz, 1H), 6.84~6.74 (m, 5H), 6.33~6.21 (m, 6H), 6.16 (s, 1H), 5.81 (d, J=9.68 Hz, 1H); $^{19}$F-{$^1$H} NMR (470 MHz, CDCl$_3$, 294 K), δ(ppm): −58.42 (s, 3F), −58.61 (s, 3F), −108.99 (d, 13.16 Hz, 1F), −109.27 (d, J=13.16 Hz, 1F); $^{31}$P-{$^1$H} NMR (202 MHz, CDCl$_3$, 294 K), δ(ppm): 19.50 (d, J=3.43 Hz, 1P), 14.82 (d, J=3.43 Hz, 1P).

The chemical structure of the heteroleptic iridium complex A-7 was confirmed to be

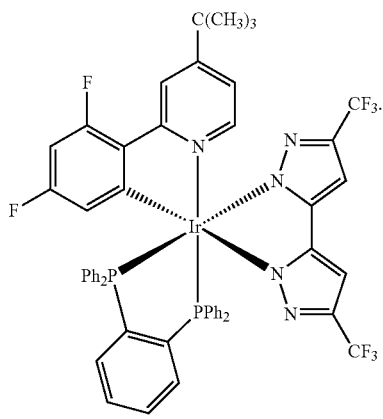

Comparative Example 1 (CE 1)

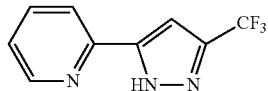

(250 mg, 1.14 mmol) and sodium carbonate (240 mg, 2.28 mmol) were disposed in a 50 ml round-bottom flask, and then 20 ml diethylene glycol monomethyl ether was added to obtain a mixture. The mixture was stirred under a nitrogen atmosphere and room temperature for 1 hour. Iridium(III) chloride hydrate (100 mg, 0.28 mmol) was then added to the mixture, and the mixture was heated under reflux for a period of 12 hours. After the reaction was completed and the temperature was reduced to room temperature, 30 ml deionized water was added to the mixture and then a white precipitate was obtained. The white precipitate was collected by suction filtration. The white precipitate was subjected to silica gel column chromatography, in which ethyl acetate was used as an eluent, followed by recrystallization from a mixture of dichloromethane and hexane to obtain a white solid (118 mg, 0.142 mmol, 50.1% yield) (hereinafter referred to as iridium complex A-8).

The spectrum analysis for the iridium complex A-8 is: $^1$H NMR (500 MHz, d$_6$-Acetone, 294 K), δ(ppm): 8.22 (td, J$_{HH}$=6.0, 0.8 Hz, 1H), 8.14~7.97 (m, 5H), 7.74 (td, J$_{HH}$=6.0, 0.8 Hz, 1H), 7.48 (td, J$_{HH}$=6.0, 0.8 Hz, 1H), 7.42 (ddd, J$_{HH}$=7.4, 5.0, 1.2 Hz, 1H), 7.34 (m, 1H), 7.31 (s, 1H), 7.28 (ddd, J$_{HH}$=7.4, 5.0, 1.2 Hz, 1H), 7.25 (s, 1H), 7.20 (ddd, J$_{HH}$=7.4, 5.0, 1.2 Hz, 1H), 7.13 (s, 1H); $^{19}$F NMR (470 MHz, d$_6$-acetone), δ(ppm): −59.80 (s, 3F), −60.00 (s, 3F), −60.05 (s, 3F).

The chemical structure of the iridium complex A-8 was confirmed to be

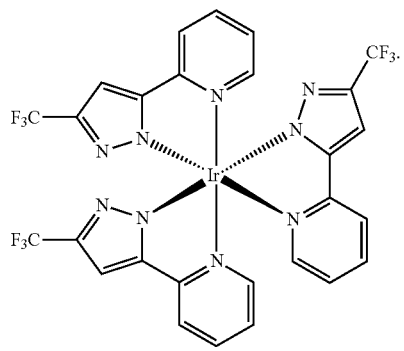

Comparative Example 2-1 (CE 2-1)

Based on the disclosure of US 2011/0282059 A1, an example of a homoleptic iridium complex of formula EM-1 disclosed therein was prepared, the example having the following formula (III) and being in a facial form.

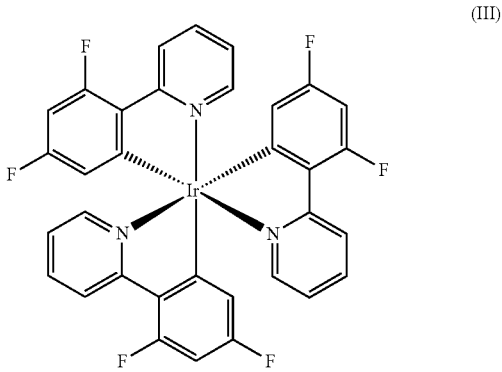

Comparative Example 2-2 (CE 2-2)

Based on the disclosure of US 2011/0282059 A1, an example of a homoleptic iridium complex having formula EM-1 disclosed therein was prepared, the example having the following formula (IV) and being in a meridional form.

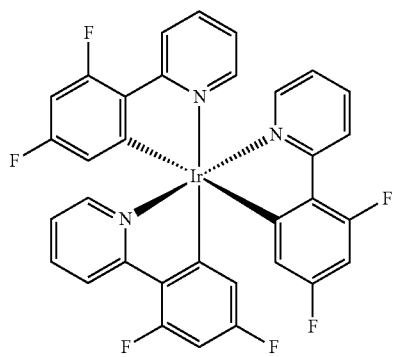

(IV)

Comparative Example 3 (CE 3)

Based on the disclosure of US 2011/0282059 A1, an example of an ionic iridium complex having formula EM-1 disclosed therein was prepared, the example having the following formula (V).

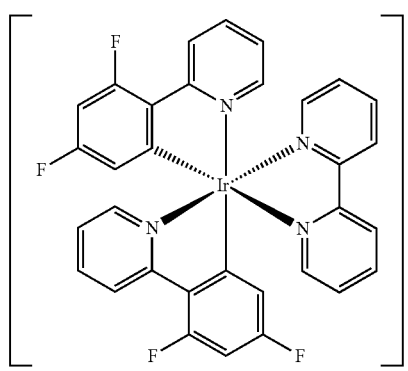

(V)

Test Items
<Absorption Wavelength>

An iridium complex was added to dichloromethane to prepare a test solution of a concentration of $10^{-5}$ M. The test solution was analyzed using a UV-Visible Spectrophotometer (Hitachi Spectrophotometer; Model no.: U-3900), and peak absorbance for a band of wavelengths between 250 nm and 700 nm was measured. The absorption wavelengths for the iridium complexes for the examples and the comparative examples are listed in the following Table 1.

<Emission Wavelength and Emission Efficiency>

An iridium complex was irradiated by light of a wavelength ranging from 340 nm to 480 nm, and was analyzed by a fluorescence spectrophotometer (Edinburgh Instruments ES920) with an integrating sphere. Emission wavelength of light emitted from the iridium complex was measured in the wavelength range of 400 nm to 900 nm. A number of photons absorbed by the iridium complex and a number of photons emitted from the iridium complex were also measured, and the emission efficiency for the iridium complex was calculated. It is noted that emission efficiency is a ratio of the number of photons emitted from the iridium complex to the number of photons absorbed by the iridium complex. The results of the emission wavelengths and the emission efficiencies for the iridium complexes of the examples and the comparative examples are listed in Table 1.

<Molecular Orbital Theory Calculation>

The highest occupied molecular orbital (HOMO) and the lowest unoccupied molecular orbital (LUMO) for an iridium complex with a specific chemical formula were calculated by density functional theory (DFT) using a calculation program, Gaussian 03. The results for the iridium complexes of Examples 1 to 4 and Comparative Example 1 are shown in FIG. 1.

TABLE 1

| | Absorption wavelength (λ, nm) | Emission wavelength (λ, nm) | Emission efficiency (%) |
|---|---|---|---|
| EX 1 | 266, 311, 434 | 532 | 70 |
| EX 2 | 277, 347, 374, 413, 490 | 566 | 20 |
| EX 3 | 280, 350, 374, 413, 490 | 588, 625 | 30 |
| EX 4 | 269, 312 | 429, 457, 480 (sh) | 32 |
| EX 5 | 317 | 419, 445, 470 (sh) | 48 |
| EX 6 | 272, 349 | 457, 186, 514 (sh) | 100 |
| EX 7 | 271, 318 | 450, 179, 508 (sh) | 84 |
| CE 1 | 259, 305 | 523 | 10 |
| CE 2-1 | 240, 274, 292, 346, 379, 427, 457 | 468 | 43 |
| CE 2-2 | 264, 312, 353, 388, 428, 456 | 482 | 5.3 |
| CE 3 | 277, 347, 374, 413, 490 | 534 | 18 |

In the processes for preparing the heteroleptic iridium complexes of Examples 1 to 7, it is not necessary to add complexing counter ion. Thus, each of the heteroleptic iridium complexes of Examples 1 to 7 is electroneutral.

From the results shown in Table 1, the heteroleptic iridium complexes of Examples 1 to 7 have physical properties (especially, emission efficiencies) comparable with those of the conventional iridium complexes. Thus, when each of the heteroleptic iridium complexes of Examples 1 to 7 serves as an adequate light-emitting material for an OLED, the OLED is anticipated to have good light-emitting efficiency.

From the results shown in FIG. 1, it is understood that the HOMO of the heteroleptic iridium complex of each of Examples 1 to 4 is located in

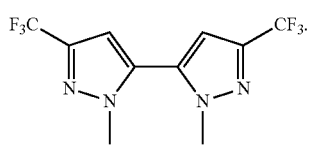 [SMILES: Cn1nc(C(F)(F)F)cc1-c1cc(C(F)(F)F)nn1C]

The LUMO of the heteroleptic iridium complex of each of Examples 1 to 3 is located in

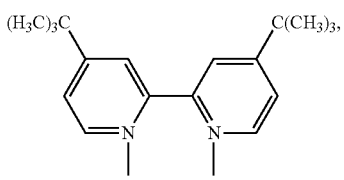

and the LUMO of the heteroleptic iridium complex of Example 4 is located in

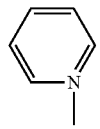

of

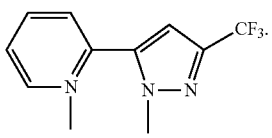

Thus, in Examples 1 to 4, an energy level of the HOMO and an energy level of the LUMO are respectively determined by different ligands of the heteroleptic iridium complex. An energy gap between the HOMO and the LUMO, which determines emission wavelength of an iridium complex and, hence, an OLED, can be determined by selection of reactants for forming ligands of the iridium complex.

The iridium complex of Comparative Example 1 is a homoleptic iridium complex, and three ligands of which are the same, i.e., each ligand is

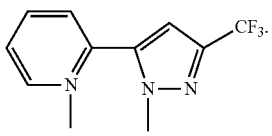

The HOMO is located in

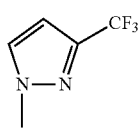

of

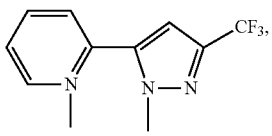

and the LUMO is located in

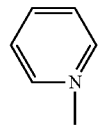

of

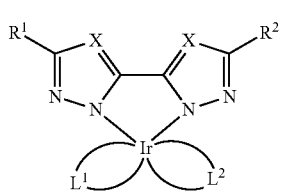

In this case, it is hard to fine-tune an energy gap between the HOMO and the LUMO because the HOMO and the LUMO are located in the same ligand, and energy levels of the HOMO and the LUMO in the same ligand would influence each other due to the fast electron transfer between ligands.

In sum, the heteroleptic iridium complex of this invention is electroneutral. An energy level of the HOMO of the complex is mainly determined by a dianionic bidentate ligand of the complex, and an energy level of the LUMO is mainly determined by a monoanionic bidentate ligand or a neutral bidentate ligand of the complex. Thus, an energy gap between the HOMO and the LUMO can be determined and adjusted by selection of reactants for forming ligands of the iridium complex. Hence, it is expected that the HOMO and LUMO levels can be easily tuned by independent and proper modification of the two different ligands respectively.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:
1. A heteroleptic iridium complex of a formula (I):

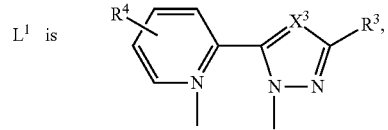

(I)

where
$R^1$ and $R^2$ are each independently hydrogen, alkyl, fluoroalkyl, or aryl,
X is $C-X^1$ or nitrogen, $X^1$ being hydrogen or phenyl, $L^1$ is 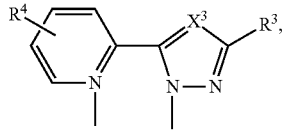, -continued

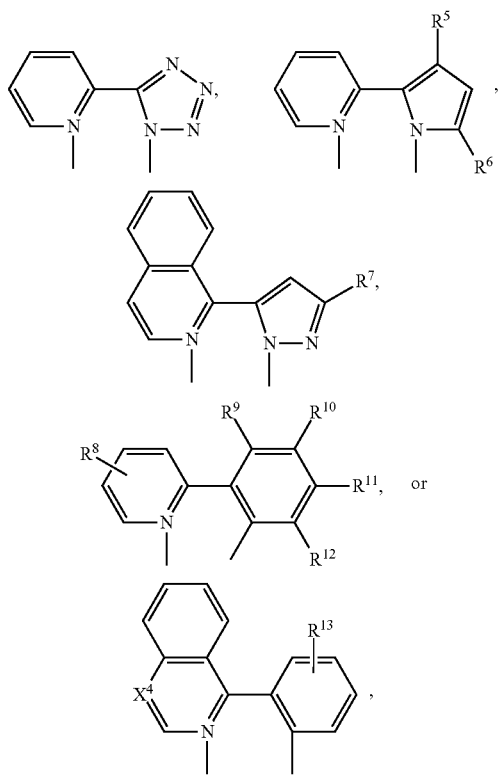

where,
R³, R⁶, R⁵, and R⁷ are each independently hydrogen, fluoroalkyl, tert-butyl, or phenyl,
R⁴, R⁸, and R¹³ are each independently hydrogen or tert-butyl,
R⁹ to R¹² are each independently hydrogen or fluorine,
X³ is nitrogen or C-X¹, and
X⁴ is C-X¹,
and L² is 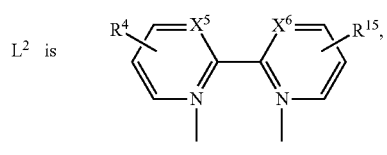

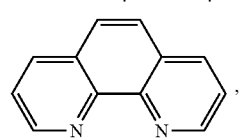

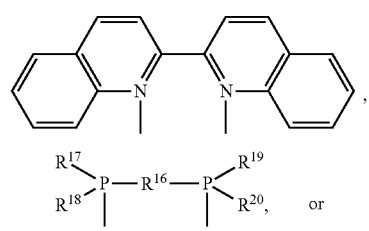

-continued

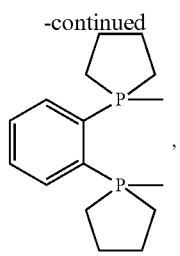

where,
R¹⁴ and R¹⁵ are each independently hydrogen or tert-butyl,
R¹⁶ is phenylene, ethylene, alkylene, or alkenylene,
R¹⁷ to R²⁰ are each independently substituted or unsubstituted phenyl, alkyl, or cycloalkyl, and
X⁵ and X⁶ are each independently C-X¹ or nitrogen.

2. The heteroleptic iridium complex of claim 1, wherein L¹ is

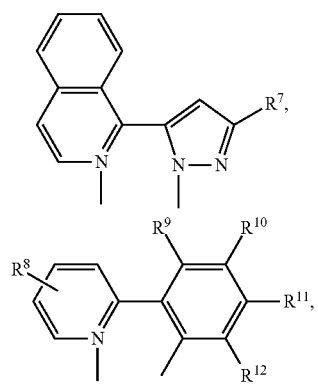

or

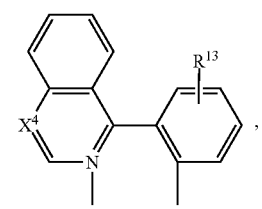

and L² is

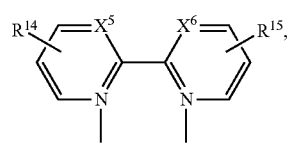

where,
R⁷ is hydrogen, fluoroalkyl, tert-butyl, or phenyl,
R⁸ and R¹³ are each independently hydrogen or tert-butyl,
R⁹ to R¹² are each independently hydrogen or fluorine,
R¹⁴ and R¹⁵ are each independently hydrogen or tert-butyl, and
X⁴, X⁵, and X⁶ are each independently C-X¹ or nitrogen.

3. The heteroleptic iridium complex of claim 1, wherein $L^1$ is

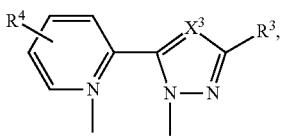

and
$L^2$ is

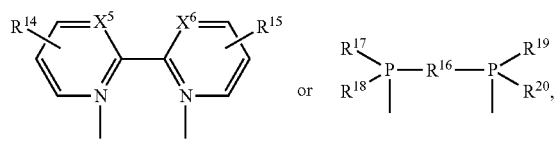

where, $R^3$ is hydrogen, fluoroalkyl, tert-butyl, or phenyl,
$R^4$ is hydrogen or tert-butyl,
$R^{14}$ and $R^{15}$ are each independently hydrogen or tert-butyl,
$R^{16}$ is phenylene, ethylene, alkylene, or alkenylene,
$R^{17}$ to $R^{20}$ are each independently substituted or unsubstituted phenyl, alkyl, or cycloalkyl,
$X^3$ is nitrogen or C-$X^1$, and
$X^5$ and $X^6$ are each independently C-$X^1$ or nitrogen.

4. The heteroleptic iridium complex of claim 1, wherein $L^1$ is

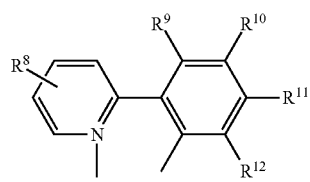

and $L^2$ is

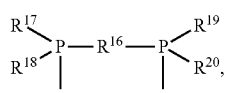

where, $R^8$ is hydrogen or tert-butyl,
$R^9$ to $R^{12}$ are each independently hydrogen or fluorine,
$R^{16}$ is phenylene, ethylene, alkylene, or alkenylene, and
$R^{17}$ to $R^{20}$ are each independently substituted or unsubstituted phenyl, alkyl, or cycloalkyl.

5. The heteroleptic iridium complex of claim 2, wherein $R^7$ to $R^{13}$ are each hydrogen, and $R^{14}$ and $R^{15}$ are each tert-butyl.

6. The heteroleptic iridium complex of claim 3, wherein $R^3$ is fluoroalkyl, $R^4$ is hydrogen, $R^{14}$ and $R^{15}$ are each tert-butyl, $R^{16}$ is phenylene, and $R^{17}$ to $R^{20}$ are each phenyl.

7. The heteroleptic iridium complex of claim 4, wherein $R^8$ is tert-butyl, $R^{16}$ is phenylene, and $R^{17}$ to $R^{20}$ are each phenyl.

8. The heteroleptic iridium complex of claim 1, wherein X is C—H, and $R^1$ and $R^2$ are each fluoroalkyl.

* * * * *